(12) United States Patent
Pendola et al.

(10) Patent No.: US 11,337,822 B2
(45) Date of Patent: *May 24, 2022

(54) TEMPOROMANDIBULAR JOINT IMPLANTS AND METHODS OF TREATING A TEMPOROMANDIBULAR JOINT

(71) Applicant: The Research Foundation for the State University of New York, Albany, NY (US)

(72) Inventors: Martin Pendola, Glendale, NY (US);
Gaia Salvadore, Brooklyn, NY (US);
Rehan Khan, Woodside, NY (US)

( * ) Notice: Subject to any disclaimer, the term of this patent is extended or adjusted under 35 U.S.C. 154(b) by 247 days.

This patent is subject to a terminal disclaimer.

(21) Appl. No.: 16/695,941

(22) Filed: Nov. 26, 2019

(65) Prior Publication Data
US 2020/0093602 A1     Mar. 26, 2020

Related U.S. Application Data

(63) Continuation of application No. 15/388,810, filed on Dec. 22, 2016, now Pat. No. 10,485,666, which is a (Continued)

(51) Int. Cl.
*A61F 2/30*     (2006.01)

(52) U.S. Cl.
CPC .. *A61F 2/3099* (2013.01); *A61F 2002/30224* (2013.01); *A61F 2002/30299* (2013.01);
(Continued)

(58) Field of Classification Search
CPC ........ A61F 2/28; A61F 2/2803; A61F 2/3099; A61B 17/8071
See application file for complete search history.

(56) References Cited

U.S. PATENT DOCUMENTS 3,707,006 A    12/1972   Bokros et al.
4,693,722 A     9/1987   Wall
(Continued)

FOREIGN PATENT DOCUMENTS

RU        2493797       9/2013
WO     2014023903       2/2014

OTHER PUBLICATIONS

International Search Report and Written Opinion of the International Searching Authority issued in PCT Application PCT/US2015/038952 dated Oct. 29, 2015.

*Primary Examiner* — Jason-Dennis N Stewart
(74) *Attorney, Agent, or Firm* — Heslin Rothenberg Farley & Mesiti P.C.; Kristian E. Ziegler, Esq.

(57) ABSTRACT

The present disclosure provides intramedullary mandibular implants for the temporomandibular joint. The mandibular implants include a stem portion, a collar portion and a head portion. The stem, collar and head portions may be integral. The stem portion may define an inferior end and the head portion may define a superior end of the implants. The head portion may be arcuate in the sagittal plane to provide an articulating surface with a fossa or a fossa component. The collar portion may be intermediate of the head and stem portions and form a channel between an interior surface of the collar portion and an exterior surface of the stem portion. In use, the stem portion may be implanted within a condyle of a mandible such that an end portion of the condyle is situated within the channel of the implant and the head portion articulates with the fossa or fossa component.

20 Claims, 11 Drawing Sheets

Related U.S. Application Data continuation of application No. PCT/US2015/038952, filed on Jul. 2, 2015.

(60) Provisional application No. 62/020,103, filed on Jul. 2, 2014.

(52) U.S. Cl.
CPC ............... *A61F 2002/30593* (2013.01); *A61F 2002/30878* (2013.01); *A61F 2002/30991* (2013.01)

(56) References Cited

U.S. PATENT DOCUMENTS

| | | |
|---|---|---|
| 4,917,701 A | 4/1990 | Morgan |
| 5,405,393 A | 4/1995 | Falkenstrom |
| 5,549,680 A | 8/1996 | Gordon |
| 6,008,432 A | 12/1999 | Taylor |
| 6,132,466 A | 10/2000 | Hoffman et al. |
| 6,582,715 B1 | 6/2003 | Barry et al. |
| 7,947,084 B2 | 5/2011 | Link |
| 8,632,604 B2 | 1/2014 | Brooks |
| 2004/0078084 A1 | 4/2004 | Albertorio |
| 2007/0179506 A1 | 8/2007 | Hoag et al. |
| 2013/0046390 A1 | 2/2013 | Rabiner et al. |
| 2013/0060347 A1 | 3/2013 | McMinn |
| 2015/0182340 A1 | 7/2015 | Ramos et al. |

TEMPOROMANDIBULAR JOINT IMPLANTS AND METHODS OF TREATING A TEMPOROMANDIBULAR JOINT

CROSS REFERENCE

This application is a continuation of U.S. patent application Ser. No. 15/388,810 filed Dec. 22, 2016, which is a continuation of PCT Application No. PCT/US2015/038952 filed on Jul. 2, 2015, which claims priority benefit of U.S. Provisional Application No. 62/020,103 filed on Jul. 2, 2014, each of which are hereby incorporated herein by reference in their entireties.

BACKGROUND

The present disclosure generally relates to implants for, and methods relating to, temporomandibular disorders.

One aspect of the craniomandibular system is that the temporomandibular joint (TMJ) moves in synchrony with its contralateral part. The rotational and translational movements of the TMJ are supported by an intra articular disc. TMJ is thereby a bilateral synovial articulation between the condyle (rounded prominence) at the end of the mandible and the fossa (a concave depression) in the squamous portion of the temporal bone. The name of the joint is derived from the two bones which form the joint: the upper temporal bone which is part of the cranium, and the lower jawbone or mandible. The functions performed by this joint (chewing, swallowing, speaking, aesthetics, etc.) are performed with the association of several structures, such as masticatory muscles, craniomandibular ligaments, and nervous connections derived from V and VII cranial nerves. TMJ has three degrees of motion, which are activated while eating, talking, breathing, and even when changing horizontal or vertical position, producing an almost continuous functional demand on the TMJ. The volume of movement of the TMJ increases the likelyhood of pathological disorders. The effects on the TMJ due to pathological disorders usually are not apparent until later in the disease process. While RA may be the most frequent articular degenerative process of the TMJ, other articular degenerative processes can affect the TMJ, such as psoriac arthritis, systemic lupus, erythematous, gout, non-inflammatory diseases, ailments, trauma, muscle disorders, and the like. Articular degeneration of the TMJ typically leads to severe damage of the TMJ and pain. Patients may experience symptoms including deep and dull preauricular pain, headaches, myofascial pains, morning jaw stiffness, clicking, decreased bite form, difficulty in swallowing and showing, decreased jaw mobility and occlusal changes. In some scenarios, the condyle may erode, such as flatten, lose height, and/or lose volume. Further, the intra-articular pannus surrounding the articular disk may form and lead to destruction of the disk, condylar resorption and erosion of the fossa.

Degenerative disorders of the TMJ has typically been treated with anti-inflammatory drugs. However, once the temporomandibular joint has been compromised, surgical treatment is commonly a preferred or more effective option. TMJ implants have increased in demand as the amount of jaw joint and muscle disorders causing articular degenerative have increased. Current typical TMJ implants for articular degeneration face several deficiencies in both design and long-term performance. For example, evidence suggests that many of the failures of typical TMJ implants are related to defects in design and materials, rather than material fatigue as TMJ forces are relatively low (e.g., less than about 450 MPa) when compared to the strength of common implant materials (e.g., titanium or Cr—Co—Mo alloys).

Current TMJ implants or treatment devices typically mimic the "ball and socket" design of prosthetic hip implants. Specifically, current TMJ implants may consist of three components: a condylar or mandibular implant made of metal, a fossa implant made of metal or a hard plastic polyethylene, and metal screws that attach the condylar and fossa implants to the exterior surface of their corresponding bones. Many mandibular component designs are relatively similar in that they provide a plate portion for fixation to the mandible, and an articulation surface for abutment with the fossa component. The plate portion of the mandibular component is typically attached to the exterior of the mandible (i.e., lateral installation), such as against the outer lateral surface of the condyle with screws passing through fixation apertures of the plate portion.

Rotation and/or translation of the mandible with respect to the fossa (and therefore the corresponding components of current TMJ implants) is primarily provided by four muscles: the masseter, the medial pterigoid, the temporalis (activate for mouth closing), and the lateral pterygoid (activate for mouth opening). Each of the muscles apply different forces on the TMJ—and therefore to the fossa and mandibular components of typical TMJ implants. Analysis has shown that current TMJ implants cannot adequately or properly manage mechanical forces applied thereto by a patient's muscles. For example, current mandibular components and corresponding fixation screws of TMJ implants may not adequately address the stress distribution of the component.

Loads transmitted inferiorly to the top of typical mandibular components are transmitted from the mandibular component to the mandible through the screws fixing the mandibular component to the mandible. The first screw of the mandibular component in the superior-to-inferior direction is subject to the maximum stress. For example, the high von Mises stress of current mandibular components may vary between 106 and 126 MPa, and highest stress may be positioned adjacent to first screw. Common prior implants claim to compensate for the high stresses on the first screw by distributing the load over other screws. Regardless, however, the fixation screws of current TMJ implants transmit loads from the implant to the mandible bone and are the points where the maximum von Mises stresses are found. These high stresses on the fixation screws, especially on the first screw, fixing the mandibular component to the mandible commonly lead to failures of such current TMJ implants. Further, lateral installation of such exteriorly mounted mandibular components of current TMJ implants fails to provide functional ranges of motion of the joint that are similar to "normal" physiological parameters.

As a result, considering the state of the art that exists today, there is a need for better implants and methods for TMJ treatment that adequately support the stresses and loads of the temporomandibular joint to provide reliable, long-lasting treatment solutions that also allow for more functional ranges of motion.

SUMMARY OF THE INVENTION

In one aspect, the present disclosure provides for a mandibular implant. The mandibular implant includes an intramedullary stem portion, a collar portion, and a head portion. The collar portion extends substantially about the stem portion, and forms a channel between the collar portion and the stem portion. The head portion includes an arcuate external surface. The collar portion is intermediate the stem portion and the head portion. The stem portion, the collar portion and the head portion being substantially aligned.

In another aspect, the present disclosure provides for a system for replacing a temporomandibular joint. The system includes a biocompatible fossa component, a biocompatible mandibular component, an intramedullary stem portion, a collar portion, and a head portion. The biocompatible fossa component is configured to be fixed to a temporal bone. The biocompatible mandibular component is configured to be fixed to a mandible bone. The collar portion extends substantially about the stem portion, and the collar portion forms a channel between the collar portion and the stem portion. The head portion includes an arcuate external surface. The collar portion is intermediate the stem portion and the head portion.

In another aspect, the present disclosure provides for a method of treating a temporomandibular joint. The method includes forming an aperture in a condyle of a mandible. The method also includes inserting a stem portion of a mandibular implant into the aperture in the condyle. The method further includes implanting the mandibular implant in the aperture of the condyle such that an end portion of the condyle is positioned within a channel formed between the stem portion and a collar portion of the mandibular implant, and a head portion including an arcuate external surface of the mandibular implant is positioned superior to the condyle.

In another aspect, the present disclosure provides a mandibular implant including an intramedullary stem portion, a collar portion and a head portion. The collar portion extends substantially about the stem portion, and forma a channel extending between the collar portion and the stem portion about the stem portion. The head portion includes an arcuate external surface. The collar portion is intermediate the stem portion and the head portion, and the stem portion, the collar portion and the head portion are substantially aligned.

In some embodiments, the stem portion, the collar portion and the head portion are integral to each other. In some embodiments, the stem portion is configured to be implanted within a condyle of a mandible. In some embodiments, the stem portion defines a free end and is elongate between the inferior end and a superior end portion. In some such embodiments, the collar portion extends from the superior end portion of the stem portion.

In some embodiments, the collar portion includes a first portion with an outer surface that tapers outwardly as it extends in a first direction from the head portion towards the stem portion. In some such embodiments, the collar portion includes a second portion that extends from the first portion along the first direction and about the stem portion. In some such embodiments, at least the second portion of the collar portion forms the channel. In some other such embodiments, the second portion of the collar portion is ring-shaped, and wherein the stem portion is cylindrical.

In some embodiments, the stem portion defines a first axis and the collar portion defines a second axis, and wherein the first axis and the second axis are aligned. In some such embodiments, the head portion defines a third axis that is oriented substantially perpendicular to the first axis and the second axis, and wherein the head portion extends along the direction of the third axis. In some such embodiments, the arcuate external surface of the head portion extends about the third axis. In some other such embodiments, the arcuate external surface of the head portion extends linearly along the direction of the third axis.

In some embodiments, the stem portion and the collar portion define a first axis and the head portion defines a third axis oriented substantially perpendicular to the first axis, and wherein the stem portion defines a first width extending along the direction of the third axis within the range of about 2 mm to about 9 mm, the channel defines a second width extending along the direction of the third axis and about the stem portion of about 2 mm, and the head portion defines a third width extending along the direction of the third axis within the range of about 10 mm to about 15 mm. In some embodiments, the channel defines a width extending between an outer surface of the stem portion and an inner surface of the collar portion of about 2 mm and a length extending substantially perpendicular to the width of about 4 mm.

In another aspect, the present disclosure provides a system for replacing a temporomandibular joint. The system includes a biocompatible fossa component configured to be fixed to a temporal bone and a biocompatible mandibular component configured to be fixed to a mandible bone. The mandibular component includes an intramedullary stem portion, a collar portion and a head portion. The collar portion extends substantially about the stem portion, and forms a channel between the collar portion and the stem portion. The head portion includes a first arcuate external surface. The collar portion is intermediate the stem portion and the head portion.

In some embodiments, the biocompatible fossa includes a second arcuate surface configured to abut and articulate with the first arcuate external surface of the head portion. In some such embodiments, the first arcuate external surface of the head portion is defined by a first radius, and the second arcuate surface of the biocompatible fossa is defined by a second radius that is greater than the first radius. In some embodiments, the stem portion, the collar portion and the head portion are of one-piece construction.

In some embodiments, the collar portion includes a first portion with a outer surface that tapers outwardly as it extends in a first direction from the head portion towards the stem portion. In some such embodiments, the collar portion includes a second portion that extends from the first portion along the first direction and about the stem portion. In some such embodiments, at least the second portion of the collar portion forms the channel about the stem portion.

In some embodiments, the stem portion defines a first axis and the collar portion defines a second axis aligned with the first axis, the head portion defines a third axis that is oriented substantially perpendicular to the first axis and the second axis, and the head portion is elongated along the direction of the third axis. In some such embodiments, the arcuate external surface of the head portion extends at least partially about the third axis and extends linearly along the direction of the third axis for a first width.

In another aspect, the present disclosure provides a method of treating a temporomandibular joint. The method includes forming an aperture in a condyle of a mandible. The method further includes aligning a stem portion of a mandibular implant with the aperture in the condyle. The method further includes implanting the mandibular implant into the aperture of the condyle such that an end portion of the condyle extending about the stem portion is positioned within a channel of the mandibular implant formed between the stem portion and a collar portion of the implant, and such that a head portion of the implant including an arcuate external surface is positioned superior to the condyle for articulation with a fossa or fossa component.

In some embodiments, the collar portion of the implant forms a ferrule effect to the end portion of the condyle. In some embodiments, the method further includes resecting a superior tip portion of the condyle of the mandible. In some embodiments, the method further includes implanting the mandibular implant into the aperture of the condyle such that the implant is angled in the anterior-to-posterior direction as it extends into the condyle in the superior-to-inferior direction. In some such embodiments, the method further includes implanting the mandibular implant into the aperture of the condyle such that the implant is substantially parallel to the sagittal plane. In some other such embodiments, the method further includes implanting the mandibular implant into the aperture of the condyle such that the implant is angled in the lateral-to-medial direction as is extends into the condyle in the superior-to-inferior direction.

In some such embodiments, the method further includes implanting a fossa component in a temporal bone corresponding to the condyle of the mandible. In some such embodiments, the arcuate external surface of the head portion of the implant is elongated and extends linearly along a first width, and the method further includes orienting the implant such that the first width of the head portion extends in the medial-lateral direction.

These and other objects, features and advantages of this disclosure will become apparent from the following detailed description of the various aspects of the disclosure taken in conjunction with the accompanying drawings.

DRAWINGS

DETAILED DESCRIPTION

Figure 1:
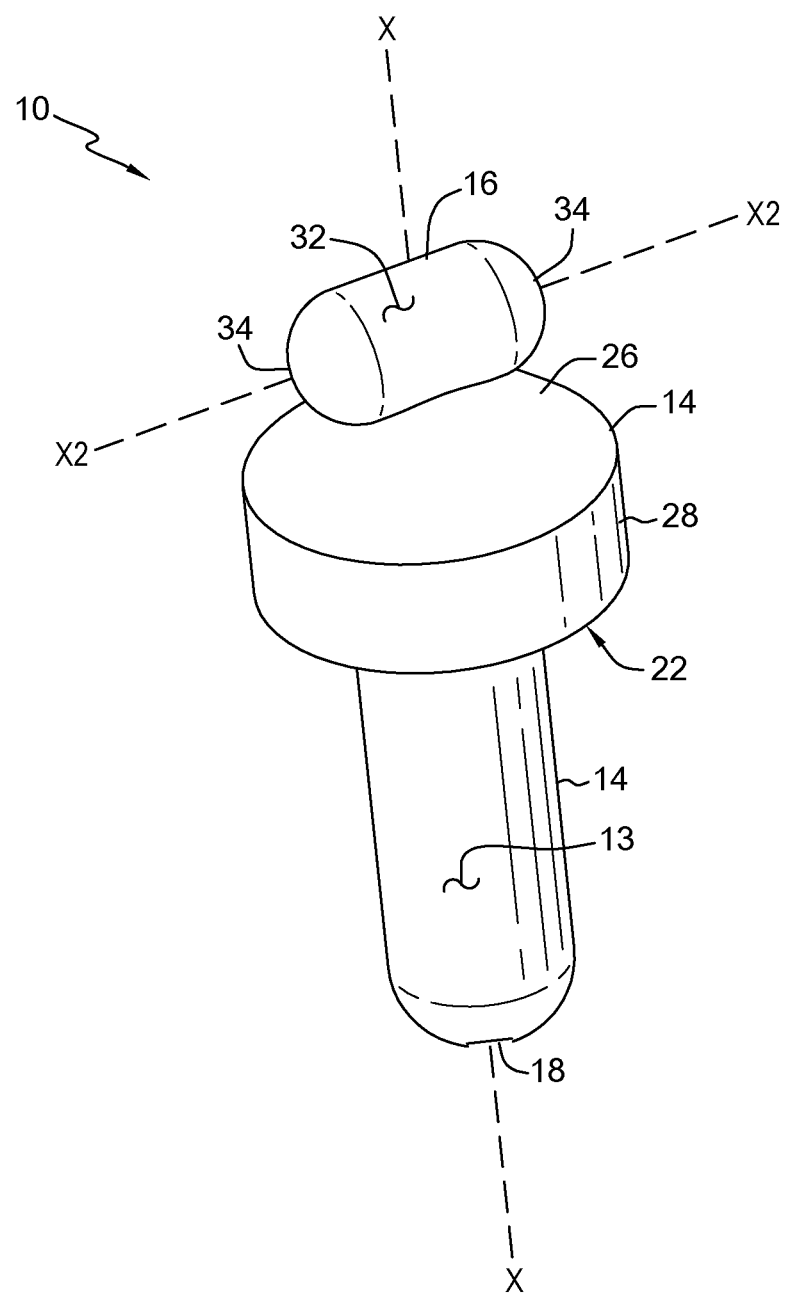
FIG. 1 is a superior perspective view of an exemplary intramedullary mandibular TMJ implant according to the present disclosure.
Figure 2:
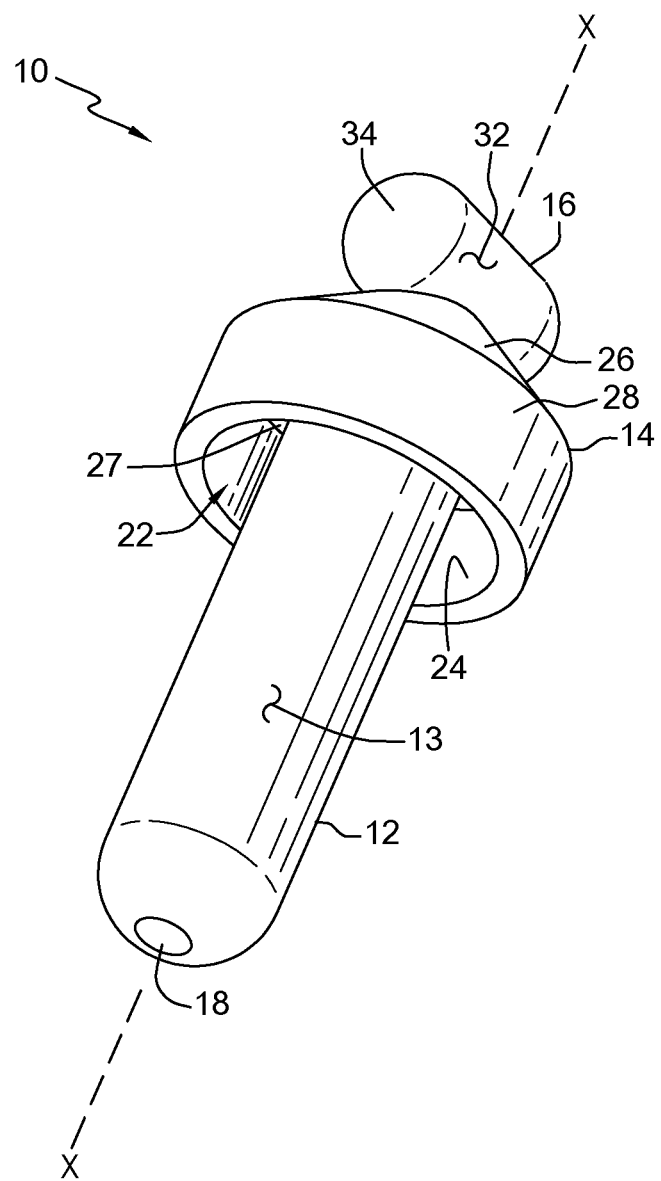
FIG. 2 is an inferior perspective view of the TMJ implant of FIG. 1.

Each embodiment presented below facilitates the explanation of certain aspects of the disclosure, and should not be interpreted as limiting the scope of the disclosure. Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles "a," "an," "the," and "said" are intended to mean that there are one or more of the elements. The terms "comprising," "including," and "having" are intended to be inclusive and mean that there may be additional elements other than the listed elements. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

In this application, including the claims, the terms proximal, distal, anterior, posterior, medial, lateral, superior, inferior, cranial and caudal are defined by their standard usage for indicating a particular aspect or orientation of a bone, other anatomy, implant, device or the like according to the relative disposition of the natural anatomy or directional terms of reference with respect thereto, as is known by ordinary skill in the art. For example, "proximal" means the portion of an implant or anatomy nearest a relative aspect, while "distal" indicates the portion of the implant or anatomy farthest from a relative aspect. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another aspect.

The present disclosure provides apparatuses, devices, systems, components and related methods of use which may facilitate motion of, and/or provide structural support to, the temporomandibular joint (hereinafter the "TMJ") via an implant. In some embodiments, the implants of the present disclosure may include an intramedullary component that is particularly advantageous for use with the mandible (i.e., a mandibular component or implant), such as with each condyle portion of the mandible. In some embodiments, the apparatus, devices, systems, components and related methods of use may include an intramedullary mandibular component and a fossa component that is fixed to the temporal bone at or about the fossa thereof. The fossa component may be configured such that a portion of the intramedullary mandibular component articulates on, or with, the fossa component, as described further below.

As shown in FIGS. 1-11, the present disclosure provides an exemplary mandibular implant or component 10 that is configured as an intramedullary component. The mandibular implant 10 is particularly configured to be situated within a condyle of the mandible, as shown in FIGS. 8-11. As shown in FIGS. 1-11, the mandibular implant 10 includes an exemplary stem portion 12, an exemplary collar portion 14, and an exemplary head portion 16. The stem portion 12, collar portion 14, and head portion 16 may be integral to each other or of one-piece construction. In some alternative embodiments, at least one of the stem portion 12, collar portion 14, and head portion 16 may be a separate and distinct component that is fixed to at least one another component, and thereby the component may be interchangeable.

The mandibular implant 10 (e.g., the stem portion 12, collar portion 14, and head portion 16) may be made from a biologically or physiologically compatible material. In some such embodiments, the mandibular component 10 (e.g., the stem portion 12, collar portion 14, and head portion 16) may be metal, carbon fiber, polymer of suitable stiffness, or combinations thereof. In some embodiments, the mandibular implant 10 may be titanium or a titanium alloy (e.g., Ti-6LV). The mandibular component 10, at least in part, may include or be formed of a material that is radiolucent. In some embodiments, the stem portion 12, collar portion 14, and head portion 16 may be made of substantially the same material (e.g., titanium or a titanium alloy).

The stem portion 12 of the mandibular implant 10 may allow the implant 10 to be situated within the mandible (i.e., intramedullary). The intramedullary stem portion 12 may be elongated and otherwise sized and/or shaped to fit within the mandible, such as into a condyle of the mandible extending at least generally in the superior-inferior direction. For example, as shown in the illustrated exemplary embodiment, the stem portion 12 may be elongate and cylindrical, such that the stem portion 12 extends substantially linearly and includes a substantially consistent shape along the length of the stem portion 12. In some alternative embodiments, the stem portion 12 may be tapered. As shown in FIGS. 1, 2 and 5-7, the stem portion 12 may define an axis X-X. The stem portion 12 may define a circular cross-section in a plane extending perpendicular to the axis X-X (i.e., form the axis X-X). In alternative embodiments, the stem portion 12 may not be cylindrical, but may include another cross-sectional shape in a plane extending perpendicular to the axis X-X. For example, the stem portion 12 may include an elliptical or oval cross-section. In some other embodiments, the stem portion 12 may include fins, ridges or other anti-rotation members. Such non-circular cross-sections and/or anti-rotation members may act to substantially prevent or limit rotation of the intramedullary stem portion 12 after implantation.

The exterior surface 13 of the stem portion 12 may be substantially smooth and arcuate, as shown in FIGS. 1-5. In some embodiments, the exterior surface 13 of the stem portion 12 may include a surface texture or material that aids in bone growth about, within or coupled to the stem portion 12 to assist in anchoring the stem portion within the mandible.

The stem portion 12 may include or define an inferior end 18 that defines the inferior end of the mandibular implant 10, as shown in FIGS. 1-4, 6, 7 and 9. The stem portion 12 may be tapered or otherwise reduce in cross-sectional area as it approaches the inferior end 18. A tapered inferior end 18 of the stem portion 12 may assist in inserting the stem portion 12, and thereby the mandibular implant 10 itself, into an aperture or passageway in a condyle of the mandible (i.e., the stem portion 12 may be configured to be an intramedullary stem portion 12). In some alternative embodiments, the inferior end 18 of the stem portion 12 may not be tapered.

Figure 7:
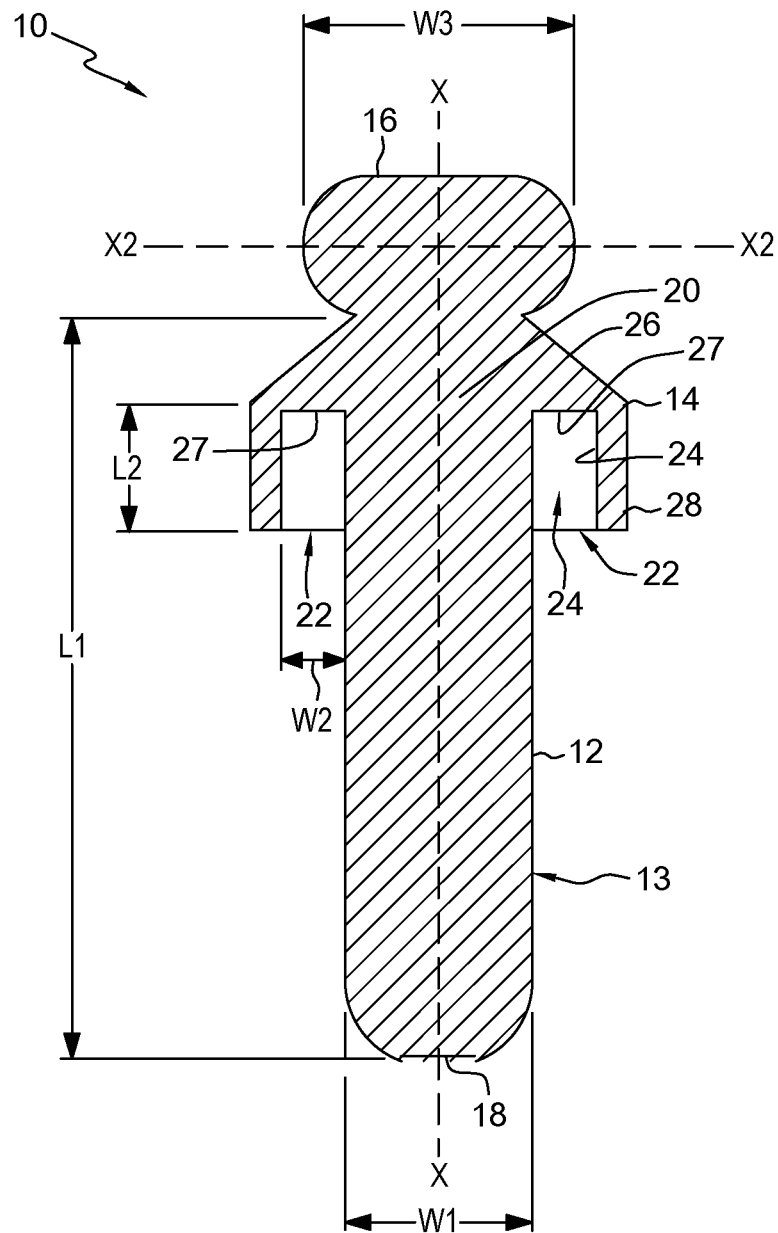
FIG. 7 is an posterior cross-sectional view of the TMJ implant of FIG. 1.
Figure 8:
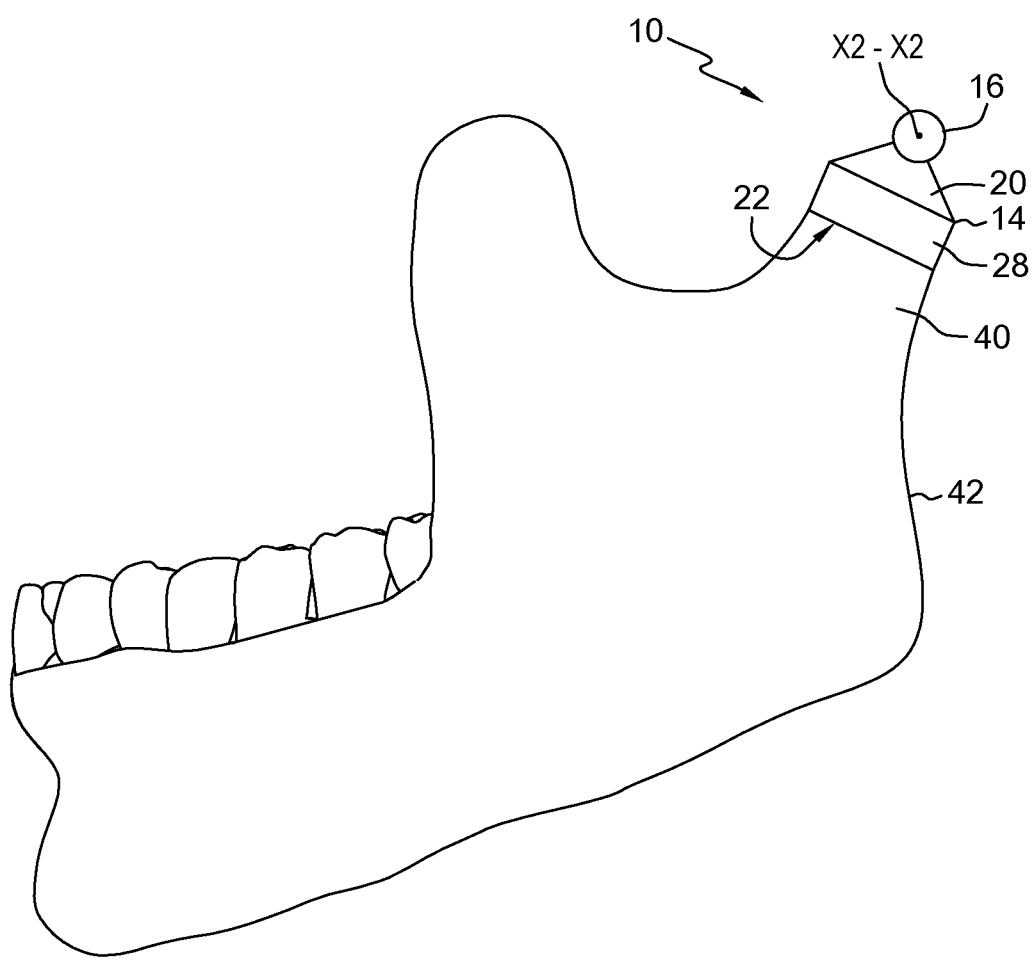
FIG. 8 is a lateral view of the TMJ implant of FIG. 1 implanted in a condyle of a mandible.

As shown in the cross-sectional view of FIG. 7, the stem portion 12 may define a length L1 (e.g., a length along the inferior-superior direction or along the axis X-X). The length L1 of the stem portion 12 may be particularly suited for use with a mandible, such as being implanted within a condyle of the mandible generally in the inferior-superior direction. In some such embodiments, the length L1 of the stem portion 12 may be within the range of about 30 mm to about 10 mm, or within the range of about 25 mm to about 15 mm. In the illustrated exemplary embodiment of FIGS. 1-11, the length L1 of the stem portion 12 is about 20 mm.

As also shown in the cross-sectional view of FIG. 7, the stem portion 12 of the mandibular implant 10 may define a width W1 (e.g., a width along the transverse plane). The width W1 of the stem portion 12 (and/or the width of other portions of the implant 10) may extend in a direction that extends substantially perpendicular to the axis X-X. In embodiments that include a cylindrical stem portion 12, the width W1 may correspond to the diameter of the stem portion 12, and one half of the width W1 may correspond to the radius of the arcuate exterior surface 13 of the stem portion 12. The width W1 of the stem portion 12 may be particularly suited for use with a mandible, such as being implanted within a condyle of the mandible. In some such embodiments, the width W1 of the stem portion 12 may be within the range of about 2 mm to about 12 mm, or within the range of about 2 mm to about 9 mm, or within the range of about 5 mm to about 9 mm. In the illustrated exemplary embodiment of FIGS. 1-11, the width W1 of the stem portion 12 is about 7 mm.

With reference to FIGS. 1-11, the collar or ferrule ring portion 14 of the of the mandibular implant 10 may be provided at an end portion 20 of the stem portion 12 that substantially opposes the inferior end 18 thereof, such as a superior end portion 20 of the stem portion 12 (as shown in the cross-sectional view of FIG. 7). As discussed above, the collar portion 14 may be integral with, or fixed to, the superior end portion 20 of the stem portion 12. The collar portion 14 may be provided or extend substantially about the stem portion 12 (e.g., about the circumference of the stem portion 12), such as substantially about the axis X-X of the stem portion 12. In some embodiments, the collar portion 14 may define an axis that is substantially aligned with the axis X-X of the stem portion 12. As such, the axis X-X may correspond to an axis of both the stem portion 12 and the collar portion 14.

As shown in FIGS. 1-11, the collar or ferrule portion 14 may extend away from the superior end portion 20 of the stem portion 12, such as along the axis X-X and/or along a direction angled with respect to the axis X-X. For example, the collar portion 14 may extend away from the exterior surface 13 of the stem portion 12 (e.g., generally in the transverse plane) and extend toward the inferior end 18 of the stem portion 12 (e.g., generally inferiorly). In this way, the collar portion 14 may form a channel, space, cavity or void 22 between an interior surface 24 of the collar portion 14 and an adjacent portion of the exterior surface 13 of the superior portion 20 of the stem portion 12 (i.e., the channel 22 may be provided about the axis X-X). The channel 22 between the collar portion 14 and the stem portion 12 may thereby extend in the transverse plane and along the superior-inferior direction. The collar portion 14 may be configured to accept a corresponding band or ring of bone within the channel 22, such as a corresponding portion of a condyle as explained further below. For example, as shown in the cross-sectional view of FIG. 7, the channel 22 may define a width W2 (e.g., a width along the transverse plane) of at least about 2 mm about the stem portion 12 to accept at least about 2 mm of a condyle bone therein.

In the exemplary embodiment shown in FIGS. 1-11, the collar or ferrule portion 14 of the mandibular implant 10 includes a first portion 26 that is substantially tapered. The exterior surface of the first portion 26 may be substantially conical in shape such that it progressively tapers or extends away from the exterior surface 13 of the stem portion 12 as it extends in a superior-to-inferior direction (e.g., along the axis X-X). Stated differently, the first portion 26 of the collar portion 14 may extend angularly away from the exterior surface 13 of the superior end portion 20 of the stem portion 12 as it extends therefrom towards the inferior end 18 of the stem portion 12. In the exemplary illustrated embodiment, the first portion 26 extends angularly away from the exterior surface 13 of the superior end portion 20 of the stem portion 12 at an angle of about 40 degrees as it extends towards the inferior end 18 to facilitate load transfer and proper seating of the implant 10 during use.

The exterior surface and/or an interior surface of the first portion 26 of the collar portion 14 may be conical in shape. In the exemplary embodiment, the first portion 26 is not spaced from the stem portion 12, but rather substantially solidly extends from the superior end portion 20 of the stem portion 12. In this way, the first portion 26 may not form at least a portion of the channel 22 other than, for example, a superior end 27 of the channel 22. However, in alternative embodiments, the first portion 26 may define an inner surface that is spaced from the stem portion 12, and thereby at least partially form the channel 22. The tapered (e.g., conical) shaped first portion 26 of the collar portion 14 may be centered about the stem portion 12, e.g., aligned with the axis X-X. For example, the first portion 26 of the collar portion 14 may define an axis that is aligned with the axis X-X.

As also shown in FIGS. 1-11, the exemplary collar or ferrule portion 14 of the mandibular implant 10 includes a second portion 28 that may extend from the first portion 26 and be spaced, at least in part, from the outer surface 13 of the stem portion 12. In this way, the second portion 28 may include or define an inner surface 24 that is adjacent and spaced from the outer surface 13 of the stem portion 12, thereby forming the channel 22 therebetween. The second portion 28 may extend from the first portion 26 of the collar portion 14 substantially in the superior-to-inferior direction. In some embodiments, the second portion 28 of the collar portion 14 may be substantially ring shaped (i.e., cylindrical and hollow). The exterior surface and/or interior surface of the second portion 28 of the collar portion 14 may be cylindrical. In some embodiments, the second portion 28 of the collar portion 14 may be centered about the stem portion 12, e.g., aligned with the axis X-X. For example, the second portion 28 of the collar portion 14 may define an axis that is aligned with the axis X-X of the stem portion 12 (and potentially also aligned with the axis of first portion 26). In this way, the inner surface 24 of the second portion 28 of the collar portion 14 may form a ring-shaped channel 22 (i.e., a hollow band) between the stem portion 12 and the second portion 12. The channel 22 may facilitate bone contact and/or load transfer during use, such as use with a condyle of a mandible. In other embodiments, the channel 22 may not be ring shaped, but may define or include an oval or other non-circular shape.

In some embodiments, the channel 22 (e.g., a ring or hollow cylindrical shaped channel 22) formed between the second portion 28 of the collar portion 14 and the superior aspect of the stem portion 12 may define a width W2 and a length L2. The width W2 may be a width along the transverse plane (e.g., along the axis X-X), and the length L2 may be a length in the superior-inferior direction (and/or perpendicular to the axis X-X). In the exemplary illustrated embodiment of FIGS. 1-11, the width W2 of the channel 22 is about 2 mm, and the length L2 of the channel 22 is about 4 mm. Such dimensions may be particularly well suited for acceptance of a tip portion of a condyle within the channel 22 to facilitate bone support and load transfer.

It is noted that the collar or ferrule portion 14 may be shaped differently, or include differing first and second portions 26, 28, than as depicted in FIGS. 1-11 to accommodate different sized and/or shaped anatomical structure. For example, the entirety of the collar or ferrule portion 14 may be conical in shape, and/or the channel 22 may be tapered and/or conical in shape (as opposed to cylindrical). The collar portion 14 may define any shape or configuration such that the collar portion 14 forms a space or channel 22 between the collar portion 14 and the stem portion 12 that extends both in the transverse plane and the inferior-superior direction, and that extends substantially about the stem portion 12 (e.g., about the axis X-X). Stated differently, the collar portion 14 may define any shape or configuration such that the collar portion 14 forms a space or channel 22 between the collar portion 14 and the stem portion 12 that is configured to accept the tip portion of a condyle of a mandible within the channel 22. As explained further below, the collar portion 14 may distribute or share forces occurring during use of the temporomandibular joint to the implant 10 (e.g., inside the implant) as opposed to the condyle, and may improve overall force stresses or loads resulting from mastication and normal jaw functions. The collar portion 14 may also prevent the condyle from splitting or splintering from the intramedullary stem portion 12 extending within the condyle.

As shown in FIGS. 1-11, the mandibular implant 10 may include a head portion 16 that is positioned at the superior end or portion of the collar portion 14. As discussed above, the head portion 16 may be integral with the collar portion 14 and/or the stem portion 12, or fixed to the collar portion 14 and/or the stem portion 12. The head portion 16 may define an end (e.g., a superior end) of the mandibular implant 10. The collar portion 14 may be positioned intermediate of the head portion 16 and the stem portion 12 in the superior-inferior direction.

The axis X-X of the stem portion 12 and the collar portion 14 may pass through the head portion 16. For example, the head portion 16 may be substantially centered on the collar portion 14 and/or stem portion 12 (e.g., substantially centered on the axis X-X). Stated differently, the stem portion 12, the collar portion 14, and the head portion 16 may be substantially aligned along the axis X-X. In some embodiments, the head portion 16 may be cylindrical such that the head portion 16 is formed about or defines axis X2-X2, as shown in FIGS. 1, 3, 4 and 7. In some such embodiments, the axis X-X of the stem portion 12 and the collar portion 14 may be substantially perpendicular to the axis X2-X2 of the head portion 16. The exterior surface 32 of the head portion 16 may be circular or elliptical in shape in the sagittal plane (e.g., extend about the axis X2-X2). In some embodiments, the head portion 16 may be kidney-shaped or otherwise configured to allow for, or provide, multi-plane range of motion with or against a fossa or fossa component, as described further below.

Figure 3:
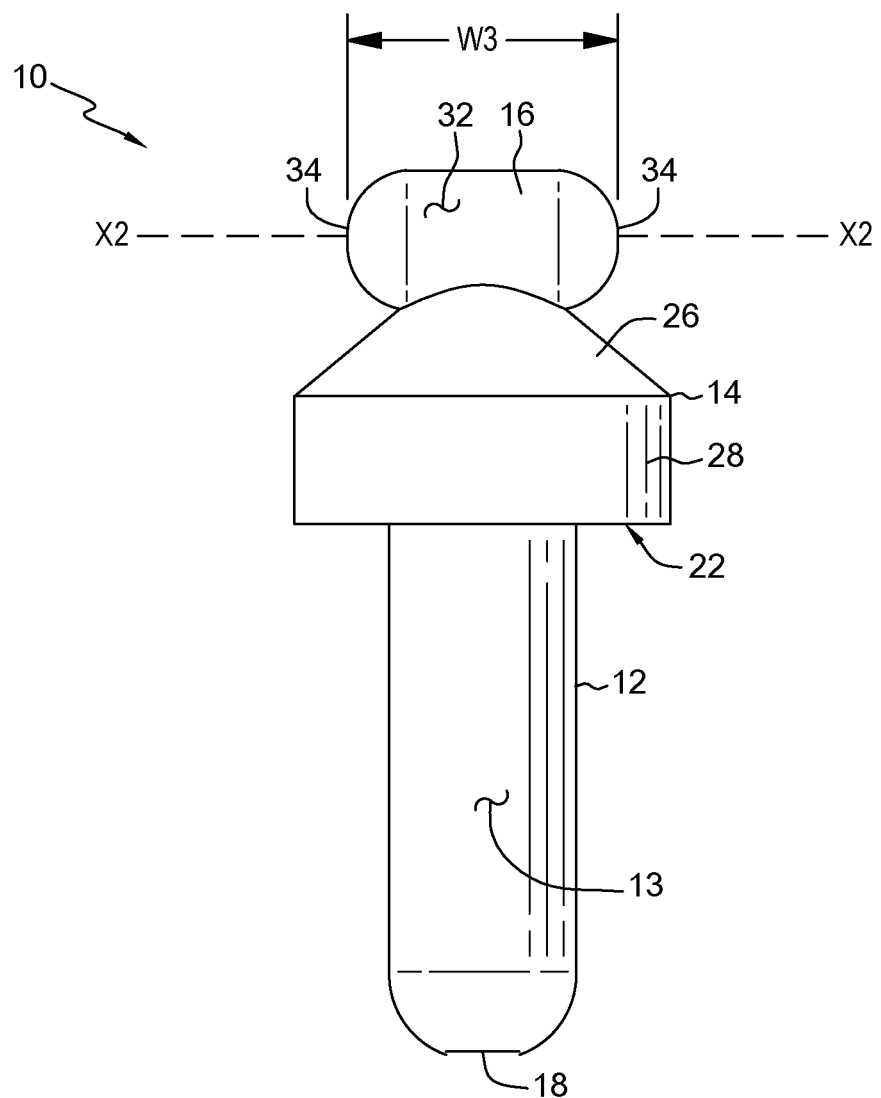
FIG. 3 is a posterior view of the TMJ implant of FIG. 1.

As shown in FIGS. 1-11, the head portion 16 may be elongated or extended in the medial-lateral direction. For example, the head portion 16 may include or define lateral ends or sides 34 in the medial-lateral direction (e.g., along the axis X-X). The lateral ends 34 of the head portion 16 in the medial-lateral direction may be arcuate or curved to form rounded or blunt ends of the head portion 16. The head portion 16 may define or include a width W3 in the medial-lateral direction between the lateral sides 34 (e.g., along the axis X2-X2), as shown in FIGS. 3 and 7. In some embodiments, the width W3 of the head portion 16 may be within the range of about 10 mm to about 15 mm, or within the range of about 11 mm to about 12 mm.

As also shown in FIGS. 1-11, at least a medial portion of the exterior surface 32 of the head portion 16 may arcuate or curved in the sagittal plane (e.g., arcuate about the axis X2-X2 extending in the medial-lateral direction). While arcuate in the sagittal plane, the arcuate exterior surface 32 may be elongated or extend linearly in the medial-lateral direction (at least in a medial portion of the head portion 16) between the lateral ends 34. In some embodiments, the arcuate exterior surface 32 may extend parallel to the axis X2-X2. In this way, the cylindrical (i.e., elongate and arcuate) exterior surface 32 of the head portion 16 may provide a stable rotational joint surface for rotation and/or translation with a fossa or fossa component (as explained further below).

Figure 4:
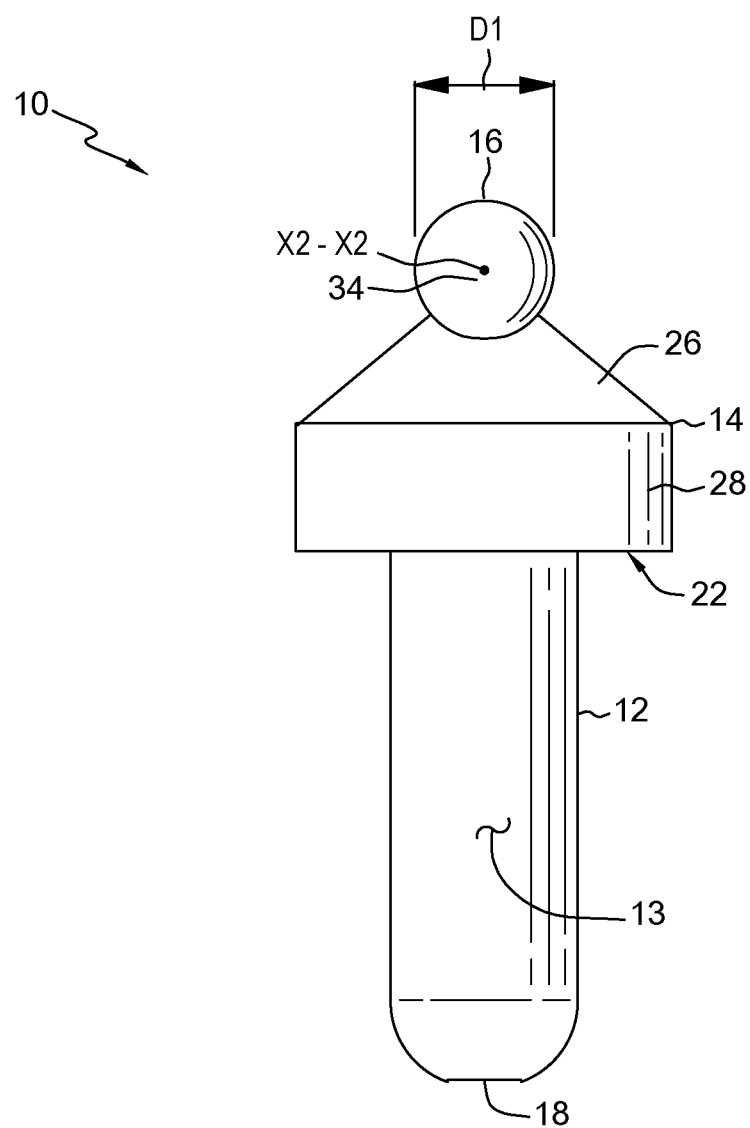
FIG. 4 is a lateral view of the TMJ implant of FIG. 1.
Figure 5:
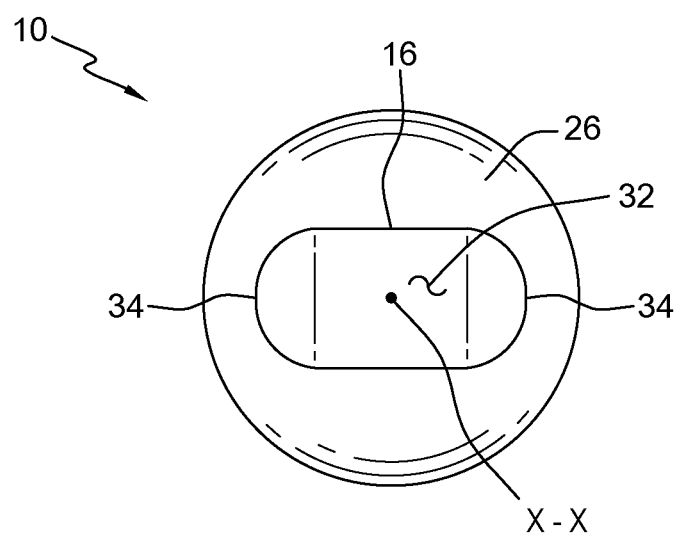
FIG. 5 is a superior view of the TMJ implant of FIG. 1.
Figure 6:
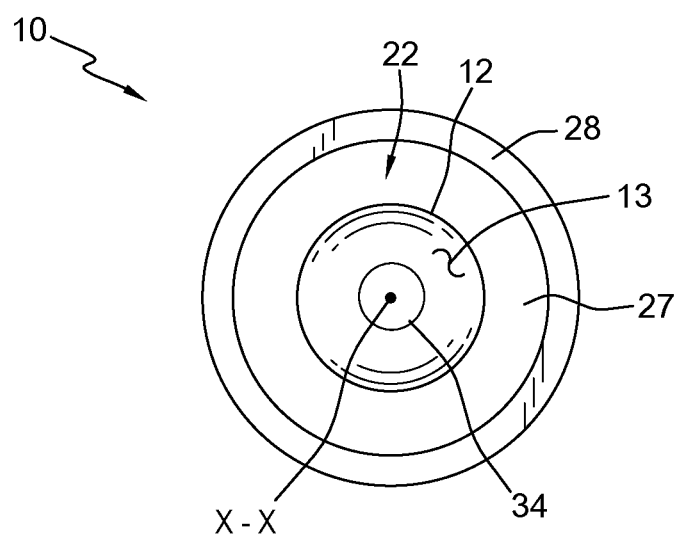
FIG. 6 is an inferior view of the TMJ implant of FIG. 1.

As shown in FIG. 4, the head portion 16 may define a depth D1 in the posterior-anterior direction (e.g., along the axis X2-X2). In the exemplary illustrated embodiment shown in FIGS. 1-11, as the exterior surface 32 of the head portion 16 is cylindrical, the arcuate exterior surface 32 may defined by a radius (extending from the axis X2-X2) that is equal to one half of the depth D1 of the head portion 16. In some embodiments, the depth D1 of the head portion (or, potentially, twice the radius defining the exterior surface 32) may be sized or otherwise configured to provide anatomically correct positioning, rotation, articulation and/or movement of the implant 10 with respect to a temporal bone when the head portion 16 is in abutment with a fossa or a fossa component 44, as shown in FIG. 11.

Figure 9:
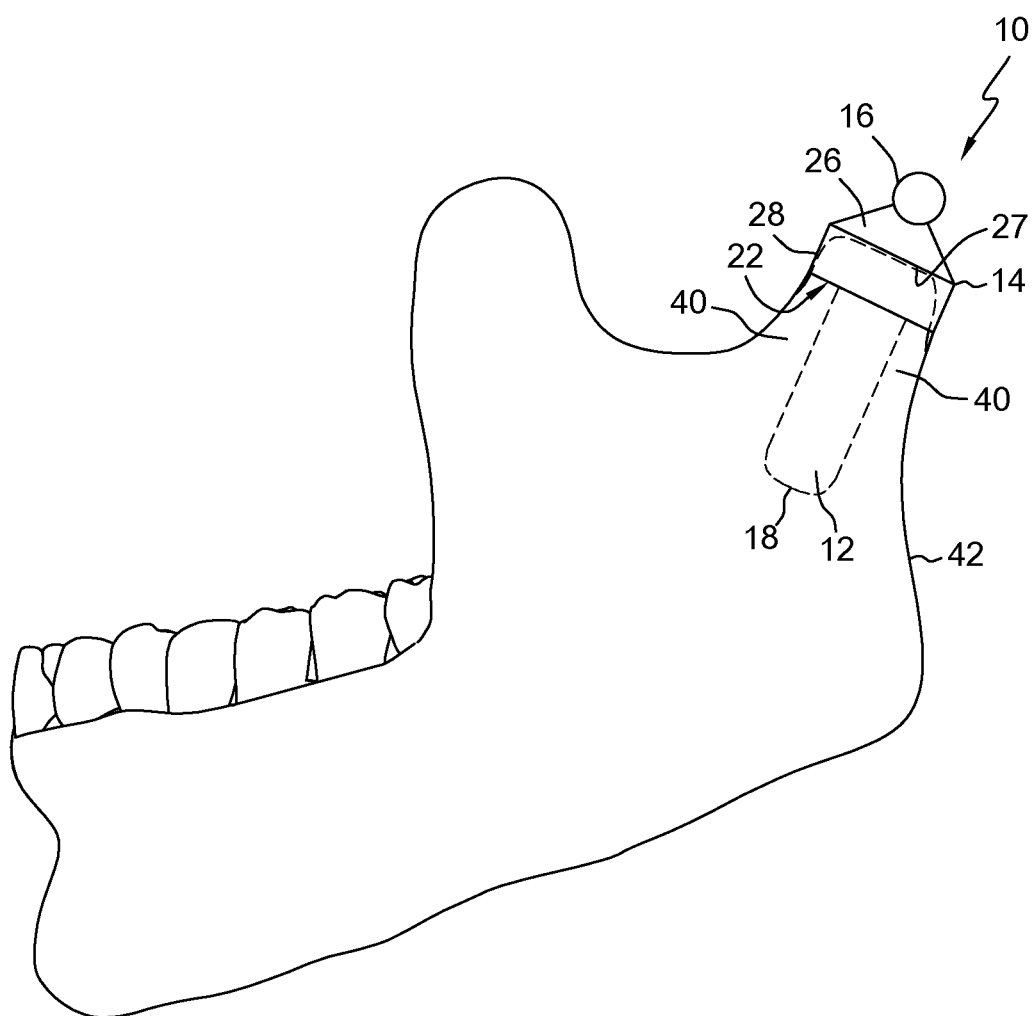
FIG. 9 is the lateral view of FIG. 8 illustrating an intramedullary stem of the implant, and a portion of the condyle positioned within a channel of the implant.

In use, as shown in FIGS. 8-11, the mandibular implant 10 may be implanted into a condyle 40 of a mandible 42 to form the mandible portion of a temporomandibular joint. Specifically, as shown in FIG. 9, the stem portion 12 of the mandibular implant 10 is inserted into an intramedullary canal of a condyle 40 of the mandible 42. The condyle 40 may be drilled or otherwise prepared for the acceptance of the stem portion 12 within the intramedullary canal. For example, the condyle 40 may be drilled or otherwise hollowed out to form an aperture or cavity that is substantially similar in size and/or shape to the stem portion 12 of the implant 10, as shown in FIG. 9.

Figure 10:
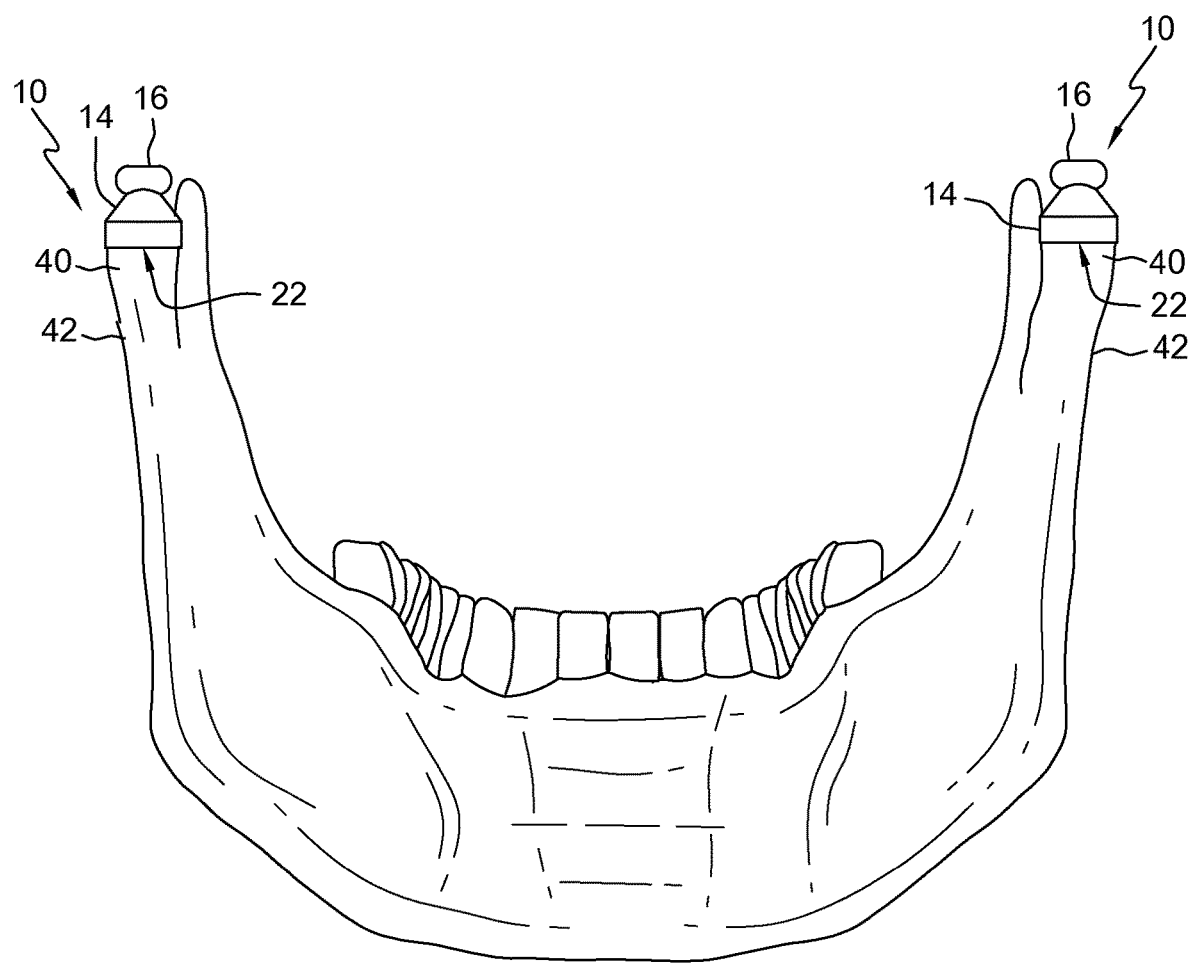
FIG. 10 is an anterior view of the implanted TMJ implant of FIG. 8.

The mandibular implant 10 may be aligned with the aperture in the condyle 40 and implanted in the condyle 40 such that the implant 10 generally extends in the superior-inferior direction from the head portion 16 to the inferior end 18 of the stem portion 12, as shown in FIGS. 8-11 (the aperture or cavity in the condyle 40 may likewise be prepared). In some embodiments, the stem portion 12 of the implant 10 may be implanted in a condyle 40 (and/or the condyle 40 likewise prepared) such that the implant 10 is angled in the anterior-to-posterior direction as is extends into the condyle 42 (i.e., as it extends in the superior-to-inferior direction), as show in FIGS. 8, 9 and 11. For example, the axis X-X of the implant 10 may be angled in the anterior-posterior direction (i.e., angled with respect to the frontal plane). As shown in FIG. 10, the stem portion 12 of the implant 10 may be implanted in a condyle 40 (and/or the condyle 40 likewise prepared) such that the implant 10 is substantially parallel to the sagittal plane, as shown in FIG. 10. In some alternative embodiments, the axis X-X of the implant 10 may be angled in the medial-lateral direction (i.e., angled with respect to the sagittal plane). For example, in some such alternative embodiments the stem portion 12 of the implant 10 may be implanted in a condyle 40 (and/or the condyle 40 likewise prepared) such that the implant 10 is angled in the lateral-to-medial direction as is extends into the condyle 42 (i.e., as it extends in the superior-to-inferior direction). The implant 10 may be oriented such that the arcuate exterior surface 32 may be extended in the medial-lateral direction (i.e., the width W3 of the head portion 16 along the axis X2-X2 extends or is elongated in the medial-lateral direction).

Figure 11:
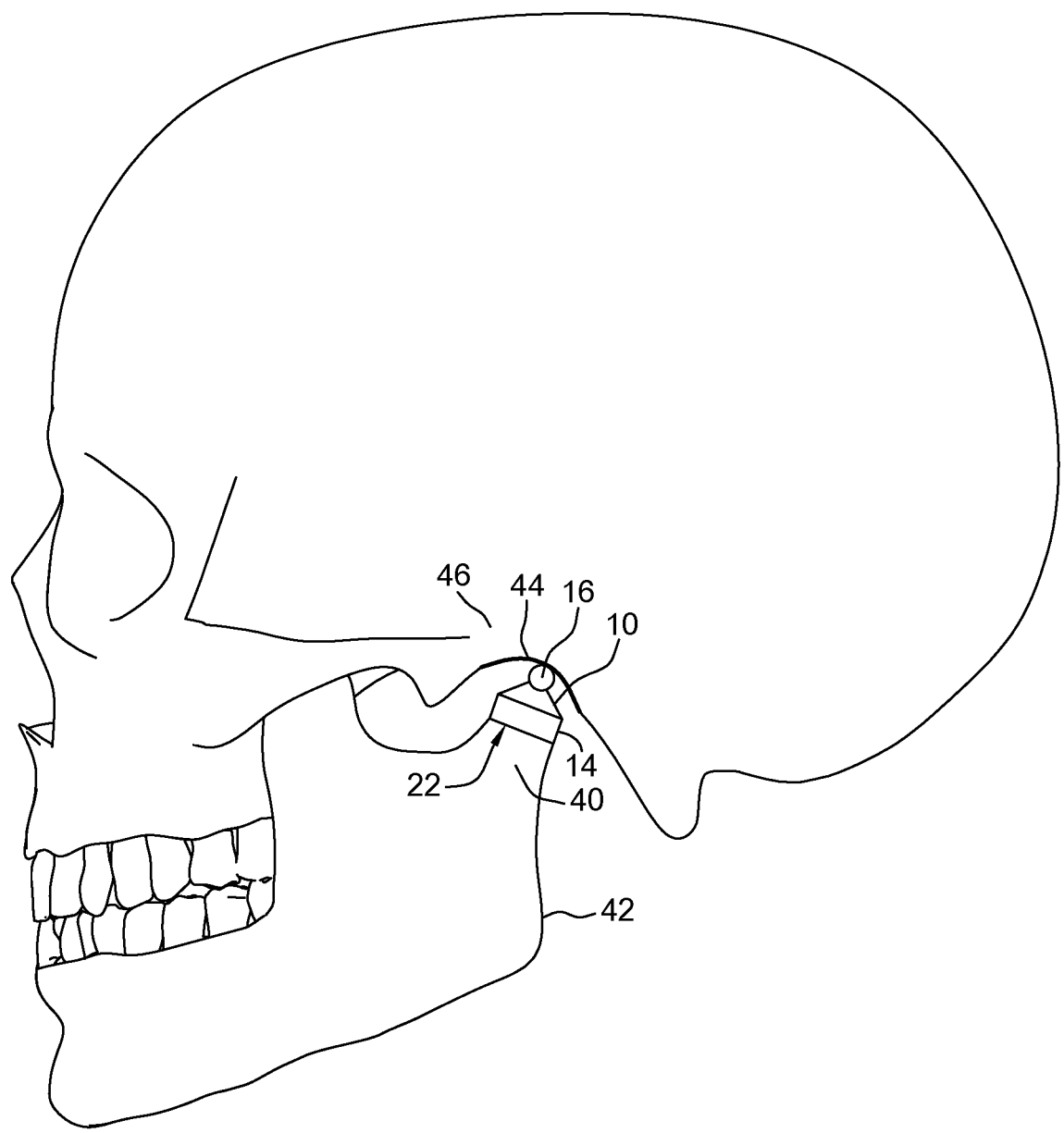
FIG. 11 is a lateral view of the implanted TMJ implant of FIG. 8 engaging a fossa or fossa component of a corresponding temporal bone.

As shown in FIGS. 8-11, the stem portion 12 of the implant 10 may be inserted within the condyle 40 generally in an superior-to-inferior direction until the end portion of the condyle 40 (extending about the stem portion 12) is seated within the channel 22 (i.e., positioned between the collar portion 14 and the stem portion 12), as illustrated in FIG. 9. The superior end of the condyle 40 may abut the superior edge or end 27 of the channel 22. In some embodiments, the superior tip portion of the condyle 40 may be resected before the implant 10 is implanted. For example, the superior tip of the condyle 40 may be shaped or formed to match the shape and/or orientation of the superior edge or end 27 of the channel 22. The superior tip portion of the condyle 40 may be resected to accommodate the length of the implant 10 extending above the condyle 40 to ensure the mandible is in its anatomically correct position with respect to the temporal bone when the head portion 16 is in abutment with the fossa or a fossa component 44, as shown in FIG. 11.

As shown in FIG. 11, after implantation of the implant (and, potentially, a fossa component 44) the arcuate surface 32 of the head portion 16 of the intramedullary implant 10 may abut and articulate with an arcuate surface of the fossa or a fossa component 44 of the temporal bone 46 after implantation. The arcuate surface of the fossa or a fossa component 44 may be defined by a radius that is greater than a radius defining the arcuate exterior surface 32 of the head portion 16. During use, the arcuate exterior surface 32 of the head portion 16 of the implant 10 is able to articulate or rotate on the arcuate surface of the fossa component 44. In this way, the implant 10 may provide a reconstructed temporomandibular joint with a range of motion substantially similar to normal anatomical parameters. After implantation, the intramedullary implant 10 may act to absorb and/or distribute stresses acting on the implant 10. For example, the intramedullary nature of the stem portion 12 of the implant, and/or the ferrule effect produced by the collar portion 14 of the implant 10, may act to distribute the stress acting on the implant 10 and condyle 40 to prevent stress concentrations (typical modes of failure) on the implant 10 and condyle 40. Further, the ferrule effect produced by the collar portion 14 of the implant may prevent the condyle 40 from splitting or splintering during installation of the implant 10 and use of the implant 10 with the fossa or a fossa component 44.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably" in conjunction with terms such as coupled, connected, joined, sealed or the like is used herein to refer to both connections resulting from separate, distinct components being directly or indirectly coupled and components being integrally formed (i.e., one-piece, integral or monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A mandibular implant, comprising:
    an intramedullary stem portion;
    a head portion including an arcuate external surface; and
    a collar portion comprising:
        a first portion comprising at least a portion that extends between the stem portion and the head portion and an outer surface portion that tapers outwardly as it extends in a first direction extending from the head portion towards the stem portion; and
        a second portion extending from the first portion and substantially about the stem portion that forms a channel between the second portion and the stem portion about the stem portion.

2. The mandibular implant of claim 1, wherein the stem portion, the first portion, the second portion and the head portion are substantially aligned.

3. The mandibular implant of claim 1, wherein a portion of the first portion extends substantially about the stem portion and forms a second channel between the first portion and the stem portion about the stem portion, the second channel cooperating with the channel between the second portion and the stem portion.

4. The mandibular implant of claim 1, wherein a bottom end portion of the outer surface portion that is adjacent to the second portion defines a width that is greater than a width of the stem portion, and wherein the second portion extends from a bottom side of the bottom end portion of the first portion.

5. The mandibular implant of claim 1, wherein the second portion defines an end surface of the channel extending between the second portion and the stem portion about the stem portion.

6. The mandibular implant of claim 1, wherein the outer surface portion tapers from a first width to a second width along the first direction, and wherein the second width is greater than a maximum width of the head portion and the stem portion.

7. The mandibular implant of claim 1, wherein the stem portion defines a free end and is elongate between an inferior end and a superior end portion.

8. The mandibular implant of claim 7, wherein the first portion extends from the superior end portion of the stem portion.

9. The mandibular implant of claim 1, wherein the second portion of the collar portion is ring-shaped, and wherein the stem portion is cylindrical.

10. The mandibular implant of claim 1, wherein the stem portion defines a first axis, the collar portion defines a second axis, and the head portion defines a third axis that is oriented substantially perpendicular to the first axis and the second axis.

11. The mandibular implant of claim 10, wherein the stem portion is elongated along the first axis, and the head portion is elongated along the third axis.

12. The mandibular implant of claim 10, wherein the first axis and the second axis are aligned.

13. The mandibular implant of claim 10, wherein the arcuate external surface of the head portion extends about the third axis.

14. The mandibular implant of claim 1, wherein the channel defines a first width extending between an outer surface of the stem portion and an inner surface of the second portion and a first length extending between a bottom edge of the second portion and an end of the channel defined by the first portion that is greater than the first width.

15. The mandibular implant of claim 1, wherein the stem portion and the collar portion define a first axis and the head portion defines a second axis oriented substantially perpendicular to the first axis, and wherein the stem portion defines a first width extending perpendicular to the first axis within the range of about 2 mm to about 9 mm, the channel defines a second width extending perpendicular to the first axis of about 2 mm, and the head portion defines a third width extending along the third axis within the range of about 10 mm to about 15 mm.

16. The mandibular implant of claim 1, wherein the stem portion, the collar portion and the head portion of the mandibular component are integral.

17. A system for replacing a temporomandibular joint, comprising:

a biocompatible fossa component configured to be fixed to a temporal bone; and a biocompatible mandibular component configured to be fixed to a mandible bone comprising:
- an intramedullary stem portion;
- a head portion including an arcuate external surface; and
- a collar portion comprising:
  - a first portion comprising at least a portion thereof that extends between the stem portion and the head portion and an outer surface portion that tapers outwardly as it extends in a first direction extending from the head portion towards the stem portion; and
  - a second portion extending from the first portion and substantially about the stem portion that forms a channel between the second portion and the stem portion about the stem portion.

18. The system of claim 17, wherein the stem portion, the first portion, the second portion and the head portion of the mandibular component are substantially aligned.

19. The system of claim 17, wherein the biocompatible fossa includes a second arcuate surface configured to abut and articulate with the first arcuate external surface of the head portion.

20. The system of claim 19, wherein the first arcuate external surface of the head portion is defined by a first radius, and the second arcuate surface of the biocompatible fossa is defined by a second radius that is greater than the first radius.

* * * * *